United States Patent [19]
Ness et al.

[11] 3,951,149
[45] Apr. 20, 1976

[54] TAPE TAB SYSTEM FOR OPENING AND REFASTENING DISPOSABLE DIAPERS

[75] Inventors: Irving Stanley Ness, Princeton; Philip Surowitz, Middlesex, both of N.J.

[73] Assignee: Johnson & Johnson, New Brunswick, N.J.

[22] Filed: Mar. 6, 1975

[21] Appl. No.: 555,910

[52] U.S. Cl. ............................ 128/287; 128/284
[51] Int. Cl.² ................ A61F 13/16; A43C 11/00
[58] Field of Search ........... 128/284, 287, 290 R, 128/156; 428/41; 117/122 D, 68.5; 24/67

[56] References Cited
UNITED STATES PATENTS

| | | | |
|---|---|---|---|
| 3,616,114 | 10/1971 | Hamaguchi | 428/41 |
| 3,620,217 | 11/1971 | Gellert | 128/284 |
| 3,642,001 | 2/1972 | Sabee | 128/287 |
| 3,646,937 | 3/1972 | Gellert | 128/287 |
| 3,848,596 | 11/1974 | Pennau | 128/284 |
| 3,853,129 | 12/1974 | Kozak | 128/287 |
| 3,874,386 | 4/1975 | Kozak | 128/287 |
| 3,875,621 | 4/1975 | Karami | 24/67 |

*Primary Examiner*—Aldrich F. Medbery

[57] ABSTRACT

An improved tape tab system for use in disposable diapers in which one end of a first strip of tape is adhesively attached to a diaper. A second strip of tape with one adhesive surface is attached to the free end of the first strip. A releasable cover strip protects the adhesive surface of the second strip. Upon diapering, the cover strip is removed from the adhesive surface of the second strip and the composite strips are fastened to an opposite corner of the diaper, the adhesive surface of the second strip making the original contact and diaper closure. The diaper may be opened for inspection or adjustment by peeling the first strip from the attached second strip, and then reclosed by repositioning the tapes in an overlapping relationship.

7 Claims, 6 Drawing Figures

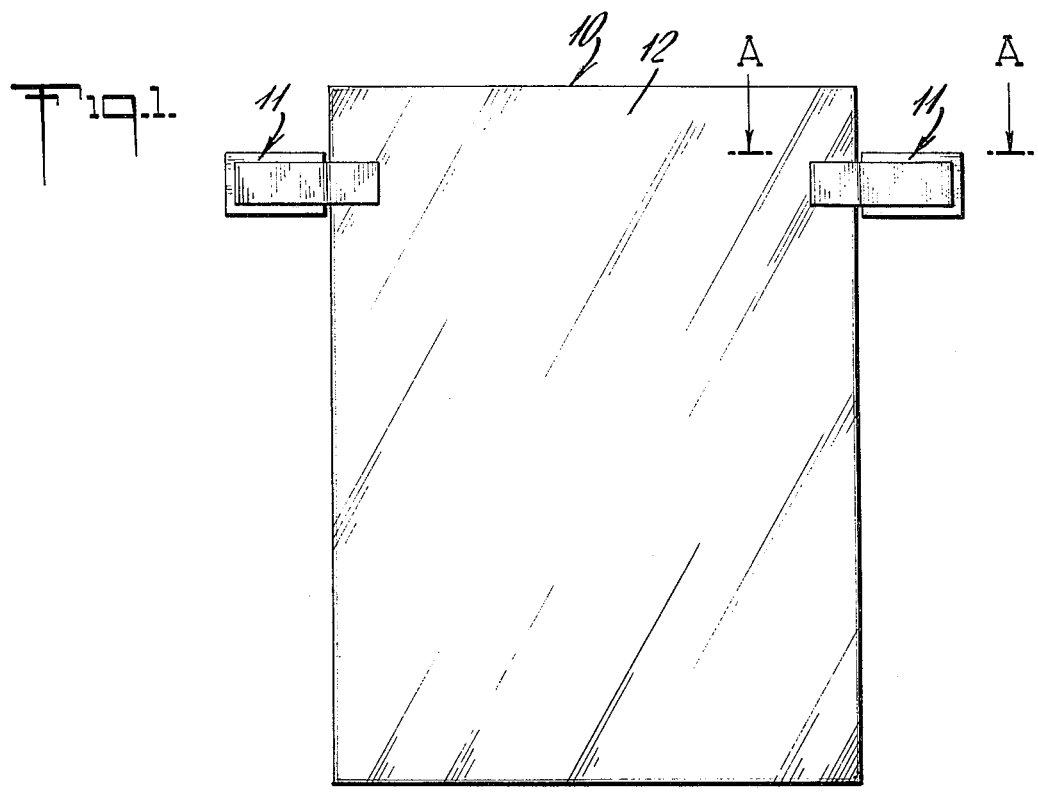
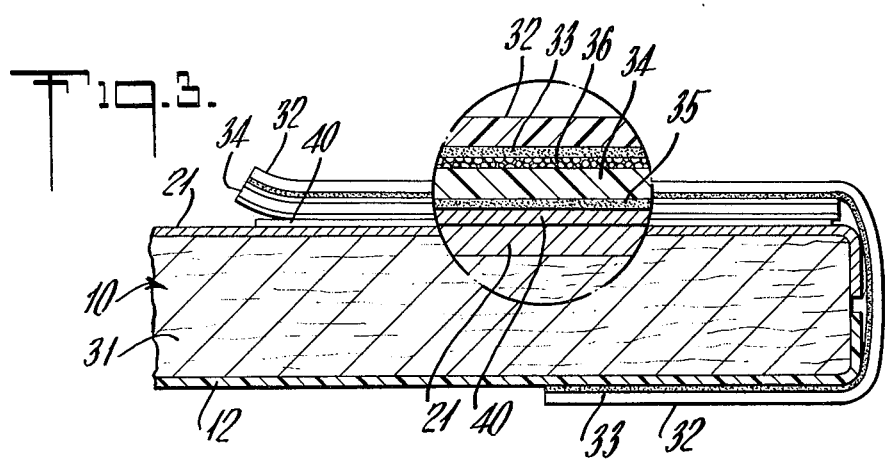
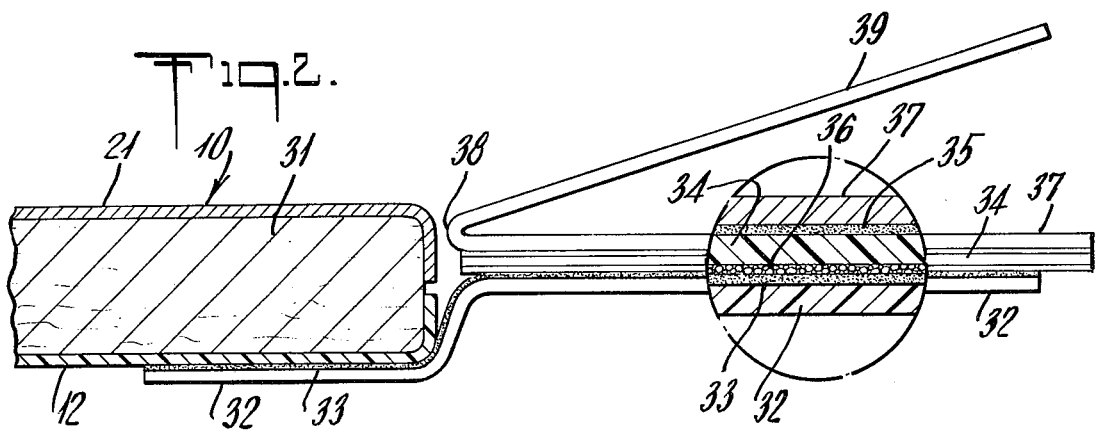

TAPE TAB SYSTEM FOR OPENING AND REFASTENING DISPOSABLE DIAPERS

This invention relates to an improved tape tab fastening system for use in disposable diapers. More particularly, this invention relates to an improved tape tab system which permits a disposable type diaper to be opened after the original closure has been made without tearing the tape tab or the surfaces of the diaper; this invention also permits refastening of the diaper; this invention also permits refastening of the diaper around the wearer while assuring a good, strong closure on subsequent fastenings.

Tape tab fastening means and arrangements have been found very practical as a way to seal disposable diapers, especially those used on infants. The tape systems have eliminated the need for pins which present problems especially when the infant is active during the diaper changing. Although tape fastening means have become a suitable substitute for pin fastening, a suitable tape tab fastening system has not been developed to simulate a pin's ability to be opened and subsequently closed. For example, when using pin fastening, if a diaper needs checking to see if the diaper has been soiled, the pin permits opening, and if no soiling is evident, the diaper is again closed about the wearer by repinning. Prior tape tab systems have not provided this flexibility. If using the known tape tabs on a disposable diaper, in order to check for soiling or for repositioning the adhesive closure cannot be broken readily. On most, if not all, occasions either the outside sheet of the diaper is torn or the tape tab itseld is torn in order to check inside. This tearing has made refastening unmanageable or impossible, thereby resulting in the loss of a possible unsoiled diaper.

Attempts have been made in tape tabs to overcome the problem of refastening a disposable diaper. For instance, in U.S. Pat. No. 3,848,596, the tape tab fastening means allows an originally fastened diaper to be opened and subsequently closed. The tape tab of that patent consists of two areas on each tab covered by two release sheets. On the first closure, only one release sheet is removed to expose pressure-sensitive adhesive. Upon adjustment or inspection, the tape is peeled from the fastened position, or the tab torn, and the other release sheet is removed, exposing fresh adhesive for a subsequent fastening. This arrangement is practical for only two fastenings, the original and one more. Also, the serious drawback of tearing the outside of the diaper when peeling off the tap remains, if the diaper does not choose to tear the tab itself. With a torn fastening area, refastening is very difficult even with a freshly exposed adhesive area on the tape.

Re-usable adhesive sealing tapes also have been employed in connecting container parts such as box flaps, paper bags and the like. In U.S. Pat. No. 3,616,114, a separable tape structure is disclosed in which a main tape is adhesively fastened to a first flap; a second tape, also attached to a first flap, is folded in partial adhesive contact with the main tape to act as a hinge for the main tape. A third tape, which may be fastened on one surface to a second flap for closure purposes, is releasably attached on the other surface to the main tape. The third tape may be omitted from the structure if the second flap surface is treated with a release agent or covered with cellophane paper, vinyl tape or the like. Not only does the folded hinge portion of the second tape make it unseparable from adhesive contact with the main tape, but it also makes it very impractical for high volume operation. Use of this type tape system in a high volume function associated with disposable diapers would result in the loss of economic advantages.

We have now discovered an improved economical tape tab system for use in disposable type diapers that permits opening an originally fastened diaper without tearing the tape tab, or, more importantly, without tearing the closure area of the diaper itself. The tape tab system of our invention is completely operable with only two tapes; there is no need to applying a coating or layer of additional material to the surface of the diaper to which it is attached for closure. Our invention also allows the diaper to be opened and closed for inspection or adjustment many times during the normal service of the diaper. Subsequent closings of the diaper, as well as the original closing around the wearer provide a good, strong adequate seal to assure containment of the bodily discharges.

In accordance with the principles of this invention, an improved tape tab system is provided for any of the well-known disposable diapers of the type having an inside surface for contact with the body of the wearer and an outside surface for direction away from the body of the wearer, and an absorbent section between the surfaces. On the outside surface, or the inside surface of the diaper, or between surfaces, a first strip of tape is attached. The first strip has adhesive material on only one surface, and is attached to the diaper so that a segment of the strip extends beyond the edge of the diaper. A second strip of tape which has adhesive material on only one surface is attached by the non-adhesive surface to the adhesive surface of the first strip. The attachment of the first and second strip. is along the segment of the first strip which extends beyond the edge of the diaper. To reduce the adhesive attachment strength between the first and second strips, the non-adhesive surface of the second strip that contacts the first strip is treated to acquire, or inherently possesses, release characteristics. The releasable surface of the second strip allows the joined strips to be detached from each other, thereby permitting openings of the diaper after an original closure has been made. The first strip is capable of bein repositioned and refastened in an overlapping relationship with the previously fastened second strip to provide subsequent diaper closings. A cover strip is releasably fastened to the adhesive surface of the second strip protecting the adhesive surface of the second strip until the diaper is ready for use.

The improved tape tab system of the present invention will allow someone inspecting or adjusting the diaper to do so many times if required during the service of the diaper. Whereas many disposable diapers had to be discarded even when unsoiled because of torn tabs or outsides, our improved system provides the economical advantage of many inspections and re-use of the diaper until soiled. It is the surprisingly good seal that can be made upon refastening the diaper and the practicality and economy of manufacture that has furnished the unexpected economical and useful advantages of the present invention.

These advantages and other features of the invention will be more easily perceived and more fully described in conjunction with the following drawings wherein:

FIG. 1 is a plan view of any well-known type disposable diaper, showing the new tape tab system attached;

FIG. 2 is an enlarged cross-sectional view of one embodiment of the new tape tab system taken along line A—A of FIG. 1;

FIG. 3 is an enlarged cross-sectional view of another embodiment of the new tape tab system showing one type of protective cover strip for the outer adhesive surface;

Figure 4:
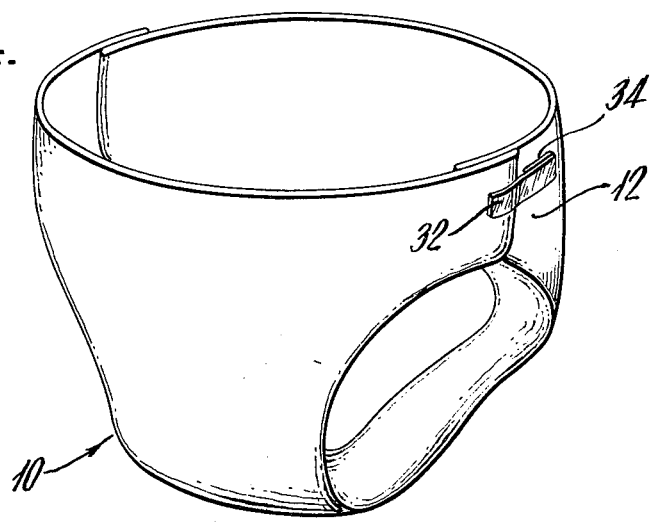
FIG. 4 is a perspective view of a diaper in a fastened condition secured with the improved tape tab system.

With particular reference to FIG. 1, there is shown a disposable type diaper 10 with an improved tape tab system 11 attached at two places to the outside surface 12 of the diaper. It is to be understood, however, for the purposes of this invention, that the tape tab system may be attached to the inside surface of the diaper, the outside surface or at some position between the surfaces, whatever is desirable. The tape tab system is depicted on the outside surface of the embodiment being described merely for purposes of relating the invention to its intended function on one suitable model.

FIG. 2 depicts one improved tape tab system 11 in detail as seen from a cross-section taken along line A—A of FIG. 1 The scale of each element has been greatly exaggerated, so that a better understanding of the tab system can be perceived. A portion of a disposable type diaper 10 having an inside surface 21, an outside surface 12 and an internal absorbent material 31 is shown with the tape tab system 11 attached. Thee system embodies a first strip of tape 32 with a layer of pressure-sensitive adhesive material 33 on one surface. One end segment of the first strip of tape is attached to the outside surface 12 of the diaper. In the embodiment shown, the first strip 32 is attached to the diaper by its adhesive surface 33. There are instances, however, when it is more desirable to adhesively treat the portion of the diaper to which the first strip is attached. In those circumstances, one end segment of the first strip 32 may be attached to the diaper either by its adhesive surface or by its non-adhesive surface. The other end segment of the first strip of tape and adhesive layer is unsecured and extends beyond the edge of the diaper.

The tape tab system includes a second strip of tape 34 with a layer of pressure-sensitive material 35 on one side. The second strip of tape 34 is attached to the unsecured, free end of the first strip of tape 32 against the surface of the first strip upon which the layer of adhesive 33 lines. The surface of the second strip of tape 34 which contacts the first strip of tape is the non-adhesive surface. The non-adhesive surface of the second strip has been treated, however, with a release agent or coating 36. The release agent 36 on the second strip acts to somewhat reduce the adhesive strength between the first and second joined strip. Even though reduced, the adhesive bond between the first and second strips is more than adequately strong to hold corners of a diaper in a closed position during use. Furthermore, the release agent 36 allows the two strips of tape to be separated without the second strip of tape pulling all the adhesive material from the first strip of tape. The release agent assuring that adhesive material will remain on the first tape, thereby allows further strong adhesive closures between the two. The release agent is applied to the non-adhesive surface of the second strip of tape in a uniformly distributed manner and acts as a coating to prevent the adhesive of the first strip from making contact with the surface of the second strip of tape. Typical release agents suitable for use in this invention are well known in the art and may be selected by those of ordinary skill to fulfill the purposes of this invention.

Instead of a release agent 36 as applied to the non-adhesive surface of the second strip 34 to provided a releasable effect, the material used as the web or tape backing of the second strip may posses inherent adhesive release qualities. For instance, the second tape may be composed of, or covered by, a continuous plastic film material or the like which furnishes a smooth, flat surface. When the adhesive of the first strip is pressed against this plastic film surface good adherence can be achieved; however, the two tapes may be easily separated since the plastic film will not retain any of the adhesive of the first tape when they are peeled from each other.

Protecting the adhesive surface of the second strip of tape is a cover strip 37. The cover strip 37 is releasably attached to the adhesive surface 35 of the second strip of tape 34. In the embodiment shown, the cover strip 37 is carried on the portion of the tapes which extends beyond the edge of the diaper. This cover strip 37 is intended to be removed from the tapes when diapering and then discarded. The cover strip may be longer than the second strip of tape and folded at 38 so that a pull-tab 39 is formed. This pull-tab 39 provides a convenient grip for the person who is diapering the wearer. When the cover strip 37 is removed the adhesive surface 35 is exposed, allowing the unsecured portion of the tape tab system to be fastened to opposite corners of the diaper which have been wrapped around the wearer.

Besides a completely removable and discardable cover strip, the cover to protect the outer adhesive surface of the second strip may be permanently fastened to the diaper. In FIG. 3, a cover strip 40 is attached to the inside surface 21 of the diaper 10. Depending on the fold of the diaper during manufacture and the desirable fold of the composite tape tab section, the cover strip may just as conveniently be fastened to the outside surface 12 of the diaper. The surface of the cover strip 40 not attached to the diaper is a release surface which will allow an adhesively treated tape to be freely separated.

In the embodiment in FIG. 3, one end of the first strip 32 with an adhesive layer 33 is attached to the diaper, in this instance the outside surface 12. The second strip of tape 34 is attached to the first stirp so that the releasably treated, non-adhesive surface 36 is contacting the adhesive layer 33. The composite layer of tapes is folded so that the outside adhesive layer 35 of the second strip is adhesively fastened against the release surface of the cover strip 40. During diapering the composite strips of tape are separated from the cover strip 40, and while the tapes are used to make the diaper closure, the cover strip 40 remains fastened to the diaper requiring no disposal.

It is to be appreciated that the release strip 40 may be any appropriate coating or material that will provide a releasable surface for an adhesive strip, and that such coating portions may be suitably located on the inside or outside surfaces of the diaper.

A fastened disposable-type diaper 10 is depicted in FIG. 4, the corners of the diaper secured with the improved tape tab system. Evident is the first strip of tape 32 adhesively attached to one corner of the diaper. The second strip of tape 34 is also evident in the fastened diaper. This tape 34 is adhesively attached to the first strip of tape through the adhesive surface of the first strip. It is the second strip of tape, however, that makes the adhesive fastening to an opposite corner of the diaper through its adhesive surface, thereby effectuating a diaper closure. When the diaper is in a fastened condition, the second strip of tape 34 actually lies between the first strip of tape 32 and the outside surface 12 of the corner of the diaper to which it is adhered. This fastening means provides a good, strong enclosure around the wearer.

Figure 5:
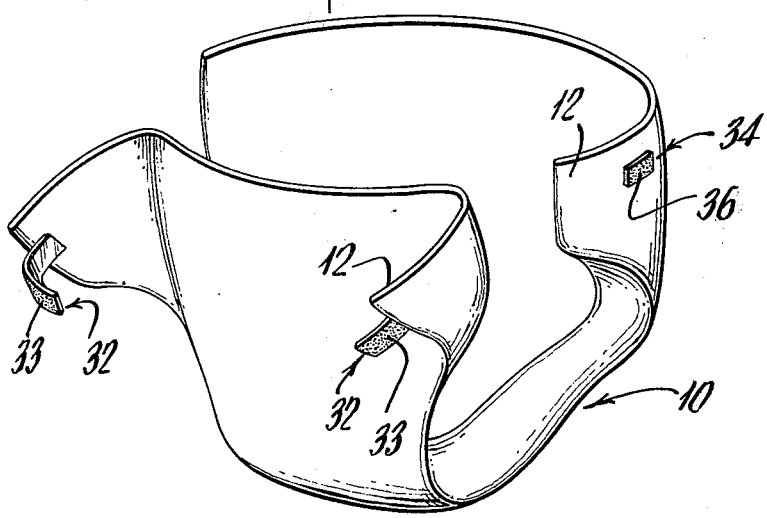
FIG. 5 is a persepctive view showing the diaper in an opened condition after the original closure has been made.
Figure 6:
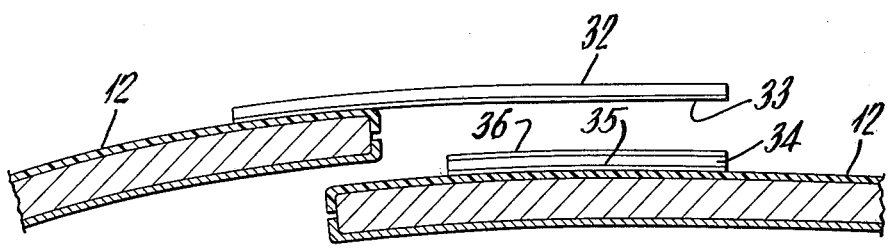
FIG. 6 is an enlarged view showing the sectional appearance of the separated tape tab elements when the diaper is in an opened condition after the original closure has been made.

The distinctive advantages and features of the improved tape tab system become apparent when viewing FIGS. 5 and 6 which show the diaper in an opened condition after an original closure has been made. When the diaper needs inspection or adjustment, the first strip of tape 32 is peeled from the second strip of tape 34. The release properties provided on the non-adhesive surface of the second strip of tape 34 facilitates the peeling. By separating the tapes a fastened diaper can be opened without resort to tearing the outside surface of the diaper or the tab itself. When separated, one end of the first strip of tape 32 remains secured to one corner of the outside surface 12 of the diaper 10, while the second strip 34 remains fastened to the opposite corner of the diaper where the original closure was made. By remaining on the diaper where the original closure was made, the second strip of tape 34 acts as a reinforcing agent; i.e., it adds strength to the area of the diaper which normally would tear upon adhesive-tap peeling since that is the point of greatest stress. The diaper is now in a condition to be inspected for soiling or to be readjusted for a better or neater fit around the wearer.

Upon completing inspection or adjustment, the diaper is wrapped around the wearer as done originally. To refasten the diaper, the first strip of tape 32 is positioned in an overlapping relationship with the second strip of tape 34 which is still attached to an opposite corner of the diaper. The adhesive surface 33 of the first strip 32 is pressed against the adhesively releasable surface 36 of the second strip 34 to complete the closure. There need not be complete overlapping alignment between the two tapes upon subsequent refastenings. Especially when adjusting the diaper after the first closure, a portion of the tapes in an overlapping relationship will furnish a sufficient closing seal.

The refastened diaper is provided with a good, strong seal due to the adhesive material that remains on the first strip after breaking the original closure. The surprising strength of subsequent closures of the diapers will permit many openings and closings of the diaper, thereby assuring practical, and more essentially, economical advantages.

Variations of the above-described embodiments of the invention may include the use of multiple tape layers above the second strip of tape on the distal portion of the tape tab system. These multiple tapes may have adhesives with suitable bonding strength in relation to each other so that consecutive tape layers may be removed singularly with successive reopenings of the tape closure.

It will be understood by those skilled in the art that other variations and modifications of the specific embodiments described above can be made without departing from the spirit and scope of the invention as defined in the appended claims.

What is claimed is:

1. In a disposable tape tab diaper having an inside surface, an outside surface and an absorbant section between said surfaces, an improved tape tab fastening system comprising: a first strip of tape with adhesive material on one surface thereof, having a segment at one end attached only to a surface of the diaper and having a second segment unattached to said surface; a second strip of tape with adhesive material on one surface thereof, the non-adhesive surface of said second strip releasably fastened to the adhesive surface to the unattached segment of said first strip; and a cover strip releasably attached to the adhesive surface of said second strip.

2. An improved tape tab fastening system as defined in claim 1 wherein the non-adhesive surface of the second strip of tape is an adhesively releasable surface.

3. An improved tape tab fastening system as defined in claim 1 wherein the non-adhesive surface of the second strip of tape has an adhesive release agent applied thereto.

4. An improved tape tab fastening system as defined in claim 1 wherein the cover strip is carried on the adhesive surface of the second strip of tape and is completely removable from the diaper.

5. An improved tape tab fastening system as defined in claim 4 wherein the cover strip if folded back in the direction over itself to form a pull-tab.

6. An improved tape tab fastening system as defined in claim 1 wherein the cover strip is permanently attached to the diaper.

7. An improved tape tab fastening system as defined in claim 6 wherein the cover strip is an adhesive release coating.

* * * * *